United States Patent
Braish et al.

[11] Patent Number: 5,929,240
[45] Date of Patent: *Jul. 27, 1999

[54] PROCESS AND INTERMEDIATES FOR PREPARING NAPHTHYRIDONECARBOXYLIC ACID SALTS

[75] Inventors: Tamim F. Braish, Ledyard; Darrell E. Fox, Pawcatuck; Timothy Norris, Gales Ferry; Peter R. Rose, Ledyard, all of Conn.

[73] Assignee: Pfizer Inc., NY, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/676,315
[22] PCT Filed: Dec. 12, 1994
[86] PCT No.: PCT/IB94/00410
§ 371 Date: Oct. 7, 1996
§ 102(e) Date: Oct. 7, 1996
[87] PCT Pub. No.: WO95/19361
PCT Pub. Date: Jul. 20, 1995
[51] Int. Cl.[6] ............... C07D 471/04; C07D 209/02
[52] U.S. Cl. ............................ 546/123; 548/452
[58] Field of Search ............... 546/123; 548/452

[56] References Cited

U.S. PATENT DOCUMENTS

| | | | |
|---|---|---|---|
| 5,164,402 | 11/1992 | Brighty | 514/300 |
| 5,256,791 | 10/1993 | Braish | 548/452 |

*Primary Examiner*—Evelyn Mei Huang
*Attorney, Agent, or Firm*—Peter C. Richardson; Paul H. Ginsburg; Lorraine B. Ling

[57] ABSTRACT

This invention relates to novel processes and intermediates for the preparation of pharmaceutically acceptable acid salts, of the formula

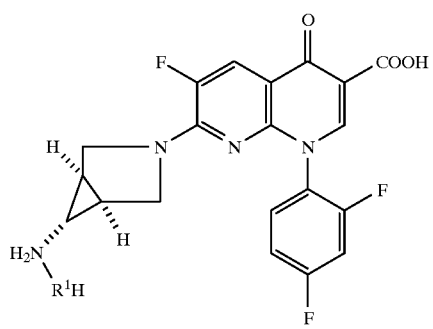

33 Claims, No Drawings

PROCESS AND INTERMEDIATES FOR PREPARING NAPHTHYRIDONECARBOXYLIC ACID SALTS

This application is the national phase of PCT/IB94/00410, filed Dec. 12, 1994, published as WO95/19361 on Jul. 20, 1995.

BACKGROUND OF THE INVENTION

This invention relates to novel processes and intermediates for the preparation of pharmaceutically acceptable acid salts, of the formula

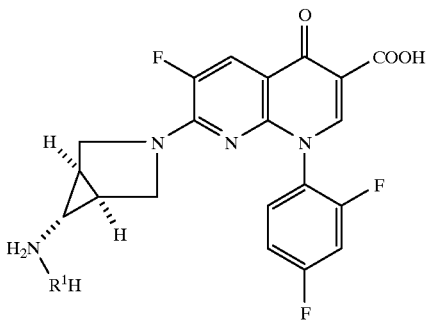

wherein $R^1H$ is a pharmaceutically acceptable acid, selected from the group consisting of $R^4SO_3H$, $R^4PO_3H$ and YH wherein $R^4$ is selected from $(C_1-C_6)$alkyl and optionally substituted phenyl or naphthyl wherein the substituent is $(C_1-C_6)$alkyl; and Y is selected from Cl, $HSO_4$, $NO_3$, $HPO_3H$, and $H_2PO_4$, of the naphthyridone antibiotic 7-(1a,5a,6a)-(6-amino-3-azabicyclo[3.1.0]hex-3-yl)-1-(2,4-difluorophenyl)-6-fluoro-1,4-dihydro-4-oxo-1,8-naphthyridine-3-carboxylic acid.

The antibacterial activity of the aforementioned naphthyridone antibiotic is described in U.S. Pat. Nos. 5,164,402 and 5,229,396 issued Nov. 17, 1992 and Jul. 20, 1993, respectively, the disclosures of which are hereby incorporated herein by reference in their entirety. The foregoing patents are assigned in common with the present application.

SUMMARY OF THE INVENTION

In a first embodiment the present invention relates to a process for preparing a compound of the formula

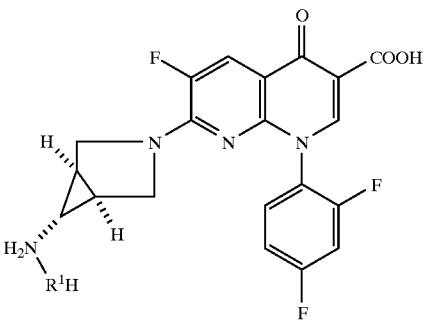

wherein $R^1H$ is a pharmaceutically acceptable acid selected from the group consisting of $R^4SO_3H$, $R^4PO_3H$ and YH wherein $R^4$ is selected from $(C_1-C_6)$alkyl and optionally substituted phenyl or naphthyl wherein the substituent is $(C_1-C_6)$alkyl; and Y is selected from Cl, $HSO_4$, $NO_3$, $HPO_3H$, and $H_2PO_4$, which comprises treating a compound of the formula

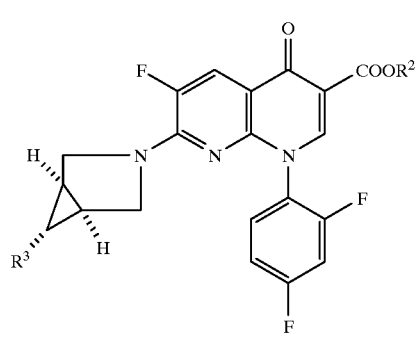

wherein $R^2$ is $(C_1-C_6)$alkyl, aryl$(C_1-C_6)$alkyl or hydrogen and $R^3$ is $NO_2$ or $NH_2$;

a) when $R^3$ is $NH_2$ with a compound of the formula $R^1H$ is as defined above; or b) when $R^3$ is $NO_2$ with a reducing agent in the presence of a compound of the formula $R^1H$ wherein $R^1H$ is as defined above.

The invention also relates to a process for preparing a compound of the formula II wherein $R^3$ is $NH_2$ and $R^2$ is as defined above by treating a compound of the formula II wherein $R^3$ is $NO_2$ with a reducing agent in the presence of a compound of the formula $R^1H$ wherein $R^1H$ is as defined above.

In another embodiment, the present invention relates to a process for preparing a compound of the formula II wherein $R^3$ is $NO_2$ comprising reacting the compound of the formula

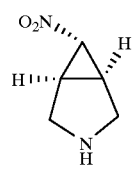

with a compound of the formula

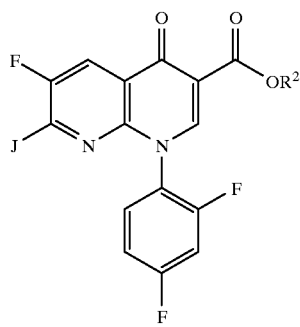

wherein $R^2$ is as defined above and J is a suitable leaving group.

In accordance with another embodiment of the invention, the compound of the formula IV is prepared by treating a compound of the formula

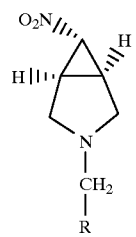

V wherein R is selected from hydrogen $(C_1-C_6)$ alkyl or $(C_6-C_{10})$aryl wherein said aryl group may be substituted, optionally, with one or more substituents independently selected from halo, nitro, $(C_1-C_6)$ alkyl, $(C_1-C_6)$ alkoxy, amino and trifluoromethyl, with an N-dealkylating agent. Preferably R is phenyl or hydrogen. The compound of formula V may be prepared by treating the compound of formula

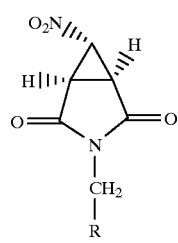

VI wherein R is as defined above, with a reducing agent. The compound of formula VI is prepared by treating a compound of the formula

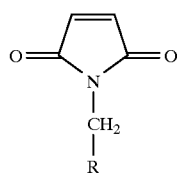

VII wherein R is as defined above, with a compound of the formula $X—CH_2—NO_2$, wherein X is a suitable leaving group, in the presence of a base. A preferred base is 1,2-dimethyl-1,4,5,6-tetrahydropyrimidine.

Yet another embodiment of the invention relates to a process for the preparation of a compound of formula I which comprises the steps of a) treating a compound of the formula VII with a compound of the formula $X—CH_2—NO_2$, wherein X is a leaving group, in the presence of a base to form a compound of the formula VI which is then treated with a reducing agent to form the compound of the formula V;

b) treating the compound of the formula V with a dealkylating agent to form the compound of formula IV;

c) treating the compound of formula IV with a compound of the formula

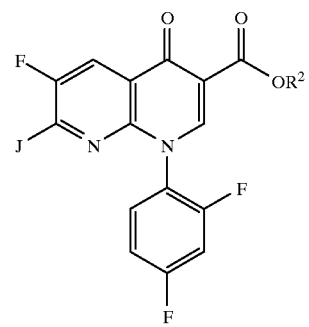

wherein $R^2$ is as defined above and J is a suitable leaving group, to form a compound of the formula II wherein $R^3$ is $NO_2$; and d) treating the compound of formula II, wherein $R^3$ is $NO_2$, with a reducing agent comprising hydrogen in the presence of a catalyst or a metal and an acid of the formula $R^1H$, as defined above, to form
i) when the hydrogenation is effected in the presence of an acid $R^1H$, as defined above, or $R^1H$ is a compound of the formula YH or $R^4SO_3H$, wherein Y and $R^4$ are as defined above, the compound of the formula I; or
ii) the compound of the formula II, wherein $R^3$ is $NH_2$, and then treating said compound with a compound of the formula $R^1H$, which may be the same as or different from the $R^1H$ of the reducing step, or a compound of the formula $R^4CO_2H$, wherein $R^4$ is defined as above, to form the compound of the formula I.

Another embodiment of the invention relates to the compound of the formula

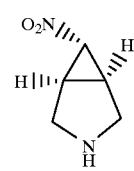

IV

Yet another embodiment of the invention relates to a compound of the formula

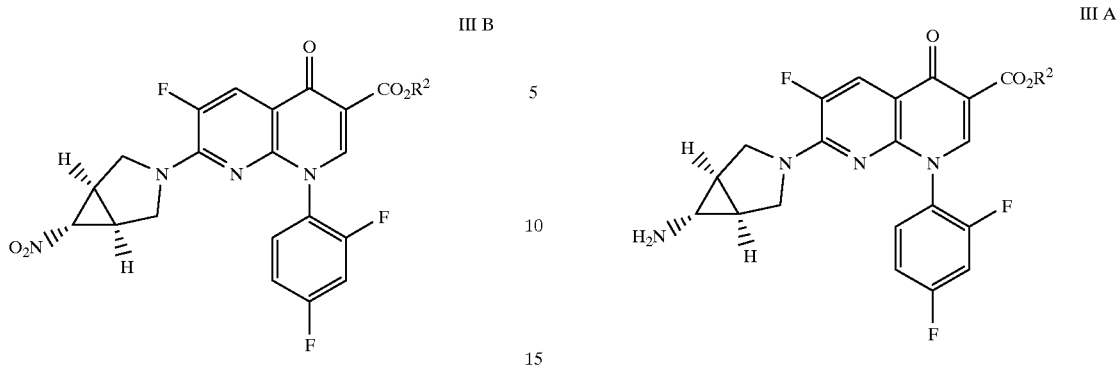

wherein R² is as defined above.

Another embodiment of the invention relates to a compound of the formula wherein R² is defined above.

The term "halo", as used herein, refers to fluoro, chloro, bromo or iodo. as applicable.

The term "alkyl", as used herein, includes straight, and when comprised of more than two carbon atoms, branched hydrocarbon chains and hydrocarbon rings and combinations of the straight or branched hydrocarbon chains with the hydrocarbon rings.

DETAILED DESCRIPTION OF THE INVENTION

The processes of the present invention and the preparation of the compounds of the present invention are illustrated in the following reaction scheme. Except where otherwise indicated, in the reaction scheme and discussion that follow substituents R,R¹H, R², R³ and X are defined as above.

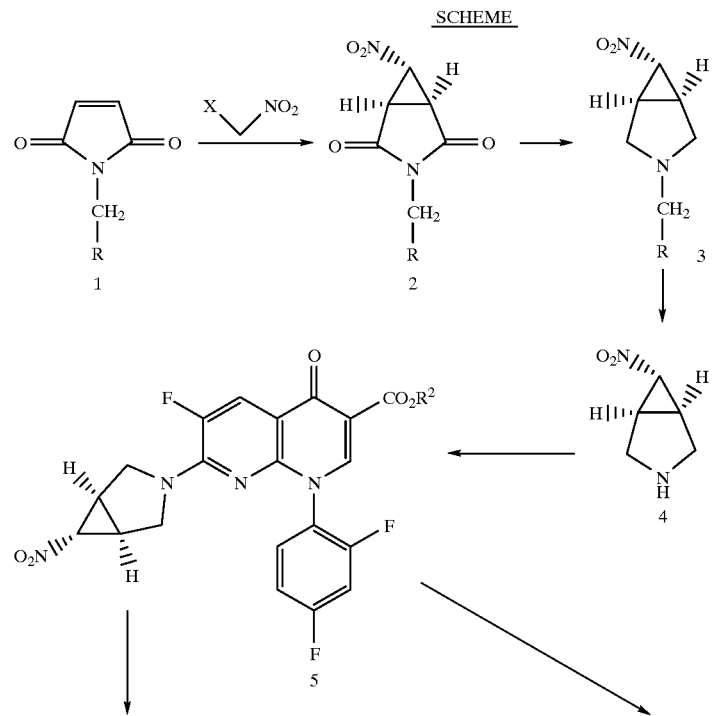

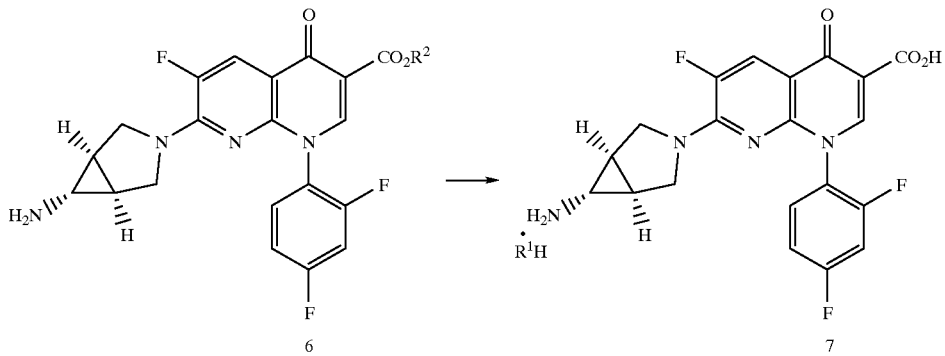

The above reaction scheme illustrates the preparation of the naphthyridone antibiotic salts of formula I, novel intermediates useful in said preparations and methods for preparing said intermediates.

Referring to the above scheme, reaction of a compound 1 with a a compound of the formula X—CH$_2$—NO$_2$, wherein X is a suitable leaving group such as chloro and bromo. in the presence of a base yields the corresponding compound 2. This reaction is generally conducted in an inert, polar, aprotic solvent such as dimethylformamide (DMF), dimethylsulfoxide (DMSO) or dimethylacetamide (DMAC), an ethereal solvent such as ethyl ether, glyme, diglyme, dioxane or tetrahydrofuran (THF) or an aromatic solvent such as optionally chlorinated benzene or toluene. Toluene is preferred. Suitable reaction temperatures range from about −78° C. to about 80° C., with about 0° C. to about −20° C. being preferred. It is preferable to add the base last. Examples of appropriate bases include carbonate bases such as potassium or sodium carbonate, phosphorine amide bases such as 2-tert-butylimino-2-diethylamino-1,3-dimethylperhydro-1,3,2-diaza-phosphorine, and amine bases such as triethylamine, guanidine, diisopropylethylamine, tetramethyl guanidine, 1,8-diazabicyclo-[5.4.0]undec-7-ene (DBU), 1,5-diazaicyclo-[4.3.0]non-5-ene (DBN) and 1,2-dimethyl-1,4,5,6-tetrahydropyrimidine. It is advantageous to use an amine base. 1,2-dimethyl-1,4,5,6-tetrahydropyrimidine is preferred.

Reduction of compound 2 in an inert ethereal solvent yields the corresponding compound 3. Appropriate reducing agents include borane, sodium borohydride and boron trifluoride•etherate complexes. Inert ethereal solvents useful in the reduction include glyme, diglyme, diisopropyl ether, dimethyl sulfide, DMSO, diethyl ether and THF. The preferred reducing agent is borane and the preferred solvents are THF or diethyl ether. The reduction is typically carried out at temperatures ranging from about 25° C. to about 90° C. It is preferably carried out in the range from about 25 to about 65° C. and most preferably in the range from about 25 to about 45° C. in THF. This method is described in U.S. Pat. No. 5,256,791, incorporated herein by reference.

Compound 3, wherein R is hydrogen, (C$_1$–C$_5$)alkyl or (C$_6$–C$_{10}$)aryl, is converted into compound 4, by treating compound 3,
 a) when R is (C$_5$–C$_{10}$)aryl with hydrogen or α-chloroethyl chloroformate; or
 b) when R is hydrogen, (C$_1$–C$_6$)alkyl with α-chloroethyl chloroformate.

When R is (C$_6$–C$_{10}$)aryl hydrogenolytic removal of the RCH$_2$ group from compound 3 is generally accomplished by reacting said compound with hydrogen gas at a pressure from about 10 psi to about 2000 psi, preferably from about 14 to about 60 psi, in the presence of a noble metal catalyst, such as palladium, platinum or rhodium, or salts thereof. Palladium, or palladium hydroxide, on carbon is preferred. The temperature may range from about 20° C. to about 80° C., and is preferably about 25° C. The solvent is usually a (C$_1$–C$_6$)alkyl alcohol and is preferably methanol.

Compound 4 is converted to compound 5 by treating it with a compound of the formula

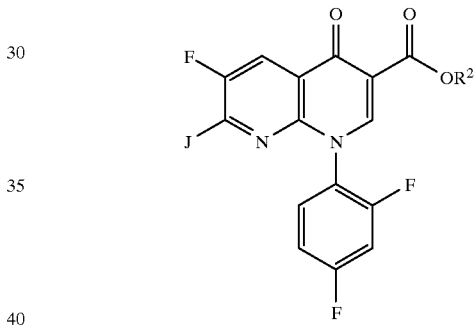

wherein R$^2$ is as defined above and J is a suitable leaving group such as chloro and bromo. A preferred leaving group is chloro or bromo and a most preferred leaving group is chloro.

The reaction may be conducted with or without a solvent. The solvent, when used, must be inert under the reaction conditions. Suitable solvents are acetonitrile, tetrahydrofuran, ethanol, chloroform, dimethylsulfoxide, dimethylformamide, pyridine, water, or mixtures thereof.

The reaction temperature usually ranges from about 20° C. to about 150° C.

The reaction may advantageously be carried out in the presence of an acid acceptor such as an inorganic or organic base, e.g. an alkali metal or alkaline earth metal carbonate or bicarbonate, or a tertiary amine, e.g. triethylamine, pyridine or picoline.

Compound 5 is converted to compound 6 by treatment with a metal and acid, of the formula R$^1$H, wherein R$^1$H is defined as above, in the presence of an aqueous aprotic solvent such as acetonitrile or DMF. The preferred metal is zinc. Suitable acids include inorganic acids, such as hydrochloric and sulfuric acids, and organic acids, such as sulfonic acids, e.g., methane-, trifluoromethane- and p-toluenesulfonic acids. Methanesulfonic acid or hydrochloric acid is preferred. This reaction is generally conducted in an aqueous (C$_1$–C$_6$)alkyl alcohol solvent, such as ethanol, methanol, 1-propanol and 2-propanol, preferably ethanol, at a temperature from about 0° C. to about 80° C., preferably at about 25° C.

Alternatively, compound 5 can be converted to 6 by treatment with hydrogen in the presence of Raney nickel or a noble metal catalyst. Raney nickel is the preferred catalyst.

The hydrogenation reaction is generally conducted in an aqueous solvent mixture. Suitable solvents include ($C_1$–$C_6$) alkyl alcohols such a ethanol, methanol 1-propanol and 2-propanol; and water miscible aprotic solvents such as DMF, THF, dimethylacetamide, dioxane, and ($C_1$–$C_6$)alkyl ethers. Hydrogen pressures used are in the range from about 14 to about 100 psi, preferably in the range about 40 to about 60 psi and temperatures are in the range of about 15° C. to about 80° C., preferably the from about 20 to about 30° C.

Compound 6 is converted to compound 7 by treatment with a compound of the formula $R^1H$, as defined as above, in an aqueous medium.

Alternatively, compound 5, may be converted directly into compound 7 by treatment with a metal and an acid of the formula $R^1H$, such as those described above, in an aqueous medium. A preferred metal is zinc and a preferred acid is methanesulfonic acid.

The pharmaceutically acceptable acid addition salts wherein the acid is a compound of the formula $R^4CO_2H$ or $R^1H$, wherein $R^4$ and $R^1H$ are defined as above, are prepared in a conventional manner by treating a solution or suspension of the free base form of compound I with about one chemical equivalent of the pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, methanesulfonic, p-toluenesulfonic, cinnamic, fumaric, phosphonic, hydrochloric, hydrobromic, hydroidic, sulfamic, and sulfonic acid.

The antibacterial compounds of formula I and the related azabicyclo naphthyridone carboxylic acid antibiotics that can be synthesized using the methods and intermediates of this invention are useful in the treatment of animals, and humans having bacterial infections. They are useful in treating bacterial infections of broad spectrum, particularly in treating gram-positive bacterial strains.

The compounds of formula I may be administered alone, but will generally be administered in a mixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously, For parenteral administration, they are best used in the form of a sterile aqueous solution which can contain other solutes, for example, enough salt or glucose to make the solution isotonic. In the case of animals, the compounds of formula I can be administered intramuscularly or subcutaneously at dosage levels of about 0.1 to about 50 mg/kg/day, advantageously about 0.2 to about 10 mg/kg/day given in a single daily dose or up to 3 divided doses.

The invention also provides pharmaceutical compositions comprising an antibacterially effective amount of a compound of the formula I together with a pharmaceutically acceptable diluent or carrier.

The compounds of the invention can be administered to humans for the treatment of bacterial diseases by either oral or parenteral routes, and may be administered orally at dosage levels of about 0.1 to 500 mg/kg/day, advantageously 0.5–50 mg/kg/day given in a single dosage or up to 3 divided dosages. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the methods and compounds of the present invention. It will be understood, however, that the invention is not limited to the specific details of these examples.

EXAMPLE 1

(1a, 5a, 6a)-3-Benzyl-6-nitro-2,4-dioxo-3-azabicyclo[3.1.0]-hexane

A 22 L vessel equipped with overhead stirrer, thermometer, dropping funnel, cooling bath, condenser, exit bubbler and nitrogen inlet was purged with nitrogen. The nitrogen purged vessel was charged with N-benzylmaleimide (500 gm, 2.67 moles), toluene (12 L), bromonitromethane (751 gm, 90%, 4.83 moles) and powdered molecular sieves (2020 gm) and stirred at about 10 to about 15° C. The slurry was treated dropwise with 1,2-dimethyl-1,4,5,6-tetrahydropyrimidine (DMTHP) (616 gm, 5.49 moles) over 3 hours. Addition of DMTHP results in a large amount of tar formation, collected on the molecular sieves. The reaction mixture was warmed to about 25° C. and stirred for 60–90 minutes. The molecular sieves were collected on a large Buchner funnel and washed twice with 2 L toluene. The filtrate was washed three times with 750 mL 2 M HCl. A 22 L vessel equipped for reflux was charged with the filtrate and Darco (Trademark) KBB (50 gm). The mixture was heated to 60–70° C. and stirred for 1 hour. The mixture was then cooled to about 25° C., filtered through a Celite (Trademark) precoated Buchner funnel, and the residue washed two times with 500 mL toluene. The carbon treated filtrate was stripped under vacuum in a 12 L round bottom flask equipped with overhead stirrer, thermometer, vacuum addition port, distillation head, condenser and 22 L receiver. Vacuum stripping was complete with about 2 to about 3 L concentrate remaining. The concentrated solution was slowly treated with 4 liters of 2-propanol. Azeotropic vacuum distillation (25° C.) was continued until toluene was no longer present ( as evidenced by a 10° C. temp. rise). The yellow orange solid was collected on a fritted funnel, washed twice with 500 mL 2-propanol and dried under vacuum at 40° C. Yield 175.38 gm (26.7%), mp 108–112° C. HPLC determined purity against an authentic sample (89–96%). $^1$H NMR (CDCl$_3$) δ 7.3(s, 5H), 4.55 (s,2H), 4.45 (s, 1H), 3.36 (s, 2H).

EXAMPLE 2

(1a,5a,6a)-6-Nitro-3-azabicyclo[3.1.0]hexane Hydrochloride

A 250 mL 3 neck round bottom flask equipped with a condenser, overhead stirrer, and dropping funnel was charged with 1,2-dichloroethane (115 mL), (1a,5a,6a)-3-benzyl-6-nitro-3-azabicyclo[3.1.0]hexane (prepared from the title compound of Example 1 by the method of Example 2 of U.S. Pat. No. 5,256,791 (incorporated herein by reference) (25.1 g, 115 mmol). The solution was cooled to about 0 to about 5° C. and treated dropwise with α-chloroethyl chloroformate (ACE—Cl) (25.3 g, 177 mmol) over 20 minutes. The reaction mixture was warmed to about 50 to about 55° C. and held for about 2 to 3 hours (reaction completion determined by TLC). The solvent and excess ACE—Cl were removed by rotary evaporation. The resulting black residue was dissolved in methanol (100 mL) and heated to about 55 to about 60° C. for 3 hours. The resultant slurry was cooled to room temperature and granulated for 18 hours. The slurry was then treated with conc. hydrochloric acid (10 mL, 115 mmol) and stirred for 1.5 hours. The product was isolated by suction filtration. The cake was washed with chloroform (25 mL) and dried under vacuum. Yield: 9.99 g, 60 mmol (53%), m.p. 170–180° C. (Dec). $^1$H NMR ($d_6$-DMSO) δ 6 9.8 (br s, 2H), 4.9 (s, 1H), 3.5 (m, 4H), 2.9 (s, 2H).

EXAMPLE 3

7-([1a,5a,6a]-6-Nitro-3-azabicyclo[3.1.0]hex-3-yl)-6-fluoro-1-(2,4-difluorophenyl)-1,4-dihydro-4-oxo-1,8-naphthyridine-3-carboxyclic Acid Ethyl Ester A 500 mL 3 neck round bottom vessel equipped with an overhead stirrer, condenser and thermometer was charged with acetonitrile (190 mL), 7-chloro-6-fluoro-1-(2,4-difluorophenyl)-1,4-dihydro-4-oxo-1,8-naphthyridine-3-carboxylic acid ethyl ester (19.07 g, 50 mmol), the title component of example 2 (9.88 g, 60 mmol), and triethylamine (15.3 g, 151 mmol). The mixture was heated to reflux (82° C.), stirred for 6.5 hours and tested for reaction completion by TLC (3:2 ethyl acetate:hexanes, UV). The resultant slurry was cooled to room temperature and treated with water (115 mL). The slurry was then granulated at about 0 to about 5° C. for 1 hour. The product was collected on a fritted funnel as a white solid and washed with 1:1 $CH_3CN$:water (50 mL). The product was dried under vacuum at 40° C. Yield: 21.17 g, 44.6 mmol (89.2%). m.p. 245–250° C. $^1$H NMR ($CDCl_3$) δ 8.4(s, 1H), 8.1 (d, 1H), 7.4 (m, 2H), 7.05 (m, 1H), 4.35 (q, 2H), 4.1 (s, 1H), 3.95 (m, 2H), 3.65 (m, 2H), 2.75 (m, 2H), 1.35 (t, 3H).

EXAMPLE 4

7-([1a,5a,6a]-6-Amino-3-azabicyclo[3.1.0]hex-3-yl)-6-fluoro-1-(2,4-difluorophenyl)-1,4-dihydro-4-oxo-1,8-naphthyridine-3-carboxyclic Acid Ethyl Ester A. A 250 mL 3 neck round bottom flask equipped with a condenser, thermometer, and overhead stirred was charged with the title compound of example 3 (10.0 g, 21.1 mmol), acetonitrile (50 mL), water (50 mL), and zinc dust (6.9 g, 105.5 mmol). The grey slurry was treated with methanesulfonic acid (70%, 25.5 mL, 241 mmol) resulting in an exotherm to 40° C. The orange-yellow reaction mixture was warmed to 50–55° C. and held for 3 hr (reaction completion by HPLC). The mixture was cooled to room temperature, treated with water (100 mL) and Celite (Trademark) (1 g), and stirred for 15 min. The slurry was filtered through a Celite precoated funnel to give a deep amber solution. The solution was basified to pH 10.1 using 50% aqueous NaOH. The orange amber slurry was treated with dichloromethane (250 mL) and filtered to remove insolubles. The organic layer was stripped to dryness yielding crude product (2.57 g, 27.4 wt %). A sample of the crude product (0.55 g) was chromatographed using a silica gel column. It was eluted seven times with 50 mL ethyl acetate and thirteen times with 50 mL methanol. The last five fractions were combined and concentrated to yield pure title compound (0.14 g, 27.2% column recovery). Overall Yield (5.73%). The product was characterized by HPLC (vs. authentic sample) and FAB MS [M+H]$^+$=445. $^1$H NMR ($CDCl_3$) δ 8.35 (s, 1H), 7.8 (d, 1H), 7.35 (m, 1H), 7.05 (m, 2H), 4.35 (q, 2H), 3.6 (br s, 2H), 3.5 (br s, 2H), 2.05 (s, 1H), 1.57 (s, 2H), 1.51 (s, 2H), 1.39 (t, 3H).

B. A 600 mL Parr (Trademark) Reactor, equipped with a Peteric Ltd. Pressflow (Trademark) Gas Controller (Model 1502), was charged with the title compound of example 3 (2.04 g, 4.3 mmol), Raney nickel [A-4000, Activated Metals and Chemicals Inc., Seviorille, Tenn.] (1.44 g wet wt.), N,N-dimethylformamide (70 mL) and water (20 mL). The reactor was sealed, purged two times with nitrogen (35 psi), charged with hydrogen (50 psi) and warmed, over 45 minutes, to about 40 to 45° C. The pressure was then increased to about 57 psi and held for 24 hours. The reaction mixture was cooled to room temperature, purged with nitrogen and tested for completion by TLC (89 $CHCl_3$: 10 methanol: 1 $NH_4OH$). The catalyst was collected through a Celite precoated funnel and was washed with water (25 mL). The filtrate to which water (40 mL) was added, extracted three times with 100 mL ethyl acetate. The ethyl acetate layer was then concentrated to 100 mL and extracted with water (100 mL) to remove residual DMF. The ethyl acetate layer was evaporated to dryness by rotary evaporation. Crude Wt. Yield: 1.36 g (71.1%). HPLC purity assay (76.5%). Purity Yield (54%). The product was characterized by HPLC (versus an authentic sample). The $^1$NMR data were the same as for the product of section A above.

C. The process of section B was repeated with a charge consisting of the title product of claim 3 (10.0 g, 21.1 mmol), Raney nickel (4.3 g wet wt.), tetrahydrofuran (THF) (180 mL) and water (40 mL). The reactor was sealed and purged two times with nitrogen (35 psi). The reactor was then charged with hydrogen (50 psi) and stirred at 25–29° C. for 2.5 hours (until hydrogen uptake ceased). The reactor was purged with nitrogen and the reaction was tested for completion by TLC (89 $CHCl_3$: 10 methanol: 1 $NH_4OH$). The catalyst was filtered off through a Celite precoated funnel. The cake was washed two times with THF (20 mL). The THF was removed by rotary evaporation to yield a pale yellow slurry. Ethanol (25 mL) was added to the slurry which was then granulated at about 20 to about 25° C. for 30 minutes. The product was isolated on a Buchner funnel. Wt. Yield: 7.56 g (80.6%). HPLC purity assay (97.1%). Purity Yield (78.3%). The product was characterized by HPLC (versus an authentic sample). The $^1$H NMR data corresponded to that of section A. A second crop 0.7 g (7.5 wt % yield) was recovered, but the purity was lower as determined by $^1$H NMR.

EXAMPLE 5

7-([1a,5a,6a]-6-Amino-3-azabicyclo[3.1.0]hex-3-yl)-6-fluoro-1-(2,4-difluorophenyl)-1,4-dihydro-4-oxo-1,8-naphthyridone-3-carboxylic Acid, Methanesulfonic Acid Salt A. A 200 mL 3 neck round bottom flask equipped with a condenser, thermometer, and overhead stirrer was charged with the title compound of the example 4 (1.54 g, 3.46 mmol) and water (25 mL). The white slurry was treated with 70% aq methanesulfonic acid (5.25, 38.4 mmol) and heated to about 45 to about 50° C. The starting material slowly went into solution. The mixture was stirred for 18 hours (tlc reaction completion). The mixture was cooled to room temperature and the product isolated by suction filtration. Yield: 1.48 g (83.5%). HPLC % purity (vs. authentic sample) 96.1%. $^1$H NMR (d$_6$-DMSO) δ 8.85 (s, 1H), 8.17 (br m, 2H). 8.11 (d, 1H), 7.83 (m, 1H), 7.62 (m, 1H), 7.37 (m, 1H), 3.67 (br s, 3H), 2.45 (s, 1H), 2.37 (s, 4H), 2.08 (s, 2H).

B. A 100 mL 3 neck round bottom flask equipped with a condenser, overhead stirrer and dropping funnel was charged with the title compound of example 3 (1.01 g, 2.13 mmol), zinc (0.70 g, 10.7 mmol), acetonitrile (20 mL), and water (20 mL). The grey slurry was warmed to about 50° C. and treated with a 5 mL of a solution of 70% aq methanesulfonic acid (3.3 g, 24 mmol). The reaction was monitored periodically, by HPLC, for completion (23 hours). The reaction was heated to about 80 to about 85° C., then treated with additional 70% aq methanesulfonic acid (2.6 g, 19 mmol) to completely hydrolyse the ester (HPLC). The reaction mixture was cooled to room temperature and treated with water (250 mL) to yield a tan slurry. The slurry was filtered and 500 mL water was added to the filtrate. The resultant solution was concentrated by rotary evaporation to remove acetonitrile. 2-Propanol (50 mL) was added to the concentrate which was then evaporated to dryness. The residue was treated with water (50 mL) and acetone (50 mL) to give a brown slurry. The slurry was filtered to remove the insolubles. The filtrate was cooled to 0 to about 5° C. to crystallize the product. Yellow crystals of title compound were obtained (105 mg, 10.5% yield). HPLC (20% CH$_3$CN: 80% pH 2, 50 mM H$_3$PO$_4$; 270 nm, 1.00 mL/min; Zorbax (Trademark) RX C$_{18}$5μ 4.6 mm×15cm) vs. standard sample of the title compound supports structure. HPLC spiking experiments with an authentic sample of the title compound demonstrated that the product of this example is the title compound. The $^1$H NMR data for the product were the same as for the product of Section A above.

We claim:

1. A process for preparing a compound of the formula

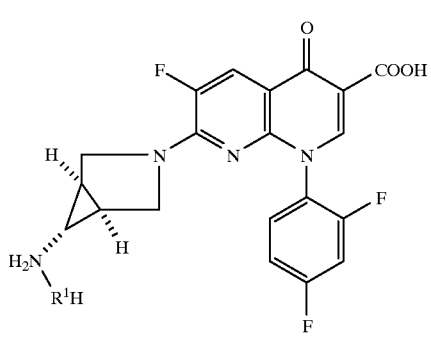

I wherein R$^1$H is a pharmaceutically acceptable acid selected from the group consisting of R$^4$SO$_3$H, R$^4$PO$_3$H and YH wherein R$^4$ is selected from (C$_1$–C$_6$)alkyl and optionally substituted phenyl or naphthyl wherein the substituent is (C$_1$–C$_6$)alkyl; and Y is selected from Cl, HSO$_4$, NO$_3$, HPO$_3$H, and H$_2$PO$_4$, which comprises treating a compound of the formula

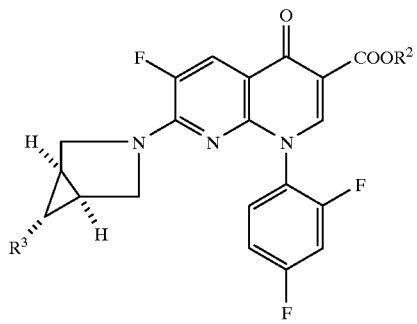

II wherein R$^2$ is (C$_1$–C$_6$)alkyl, aryl(C$_1$–C$_6$)alkyl, or hydrogen and R$^3$ is NO$_2$;

with (1) a metal and an acid of the formula R$^1$H, as defined above, to form directly the compound of formula I; or (2) a reducing agent of either (i) a metal and an acid of the formula R$^1$H, as defined above, to form the compound of the formula

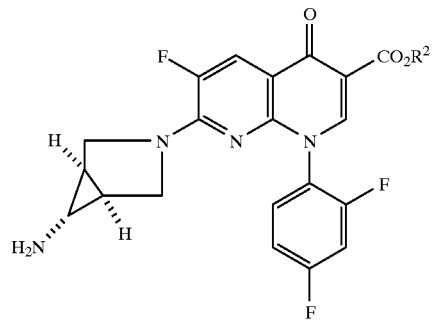

IIIA or (ii) hydrogen in the presence of a catalyst, to form the compound of the formula IIIA, and then treating the compound of the formula IIIA, formed in steps (i) or (ii) above with a compound of the formula R$^1$H, which may be the same as or different from the R$^1$H of the reducing step, to form the compound of the formula I.

2. The process of claim 1 wherein the reducing agent is hydrogen gas.

3. The process of claim 1 wherein the reducing agent is the mixture of a metal and an acid of the formula R$^1$H wherein R$^1$H is defined in claim 1.

4. The process of claim 3 wherein the metal is zinc and the acid is selected from HCl and methanesulfonic acid.

5. The process of claim 4 wherein the acid is methanesulfonic acid.

6. The process of claim 1 wherein the compound of formula II, wherein R$^3$ is NO$^2$, is prepared by reacting the compound of formula

IV

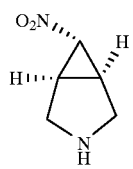

with a compound of the formula

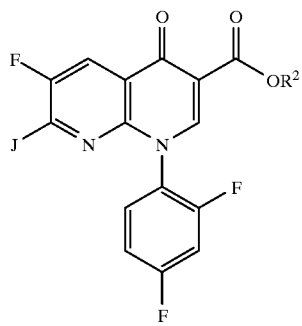

wherein $R^2$ is defined as in claim 1 and J is a leaving group.

7. The process of claim 6 wherein J is selected from chloro and bromo.

8. The process of claim 7 wherein J is chloro.

9. The process of claim 6 wherein the process is effected in the presence of an acid scavenger.

10. The process of claim 6 wherein the compound of formula IV is prepared by treating a compound of the formula

V

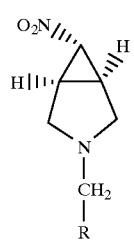

wherein R is selected from hydrogen ($C_1$–$C_6$) alkyl or ($C_6$–$C_{10}$)aryl wherein said aryl group may be substituted, optionally, with one or more substituents independently selected from halo, nitro, ($C_1$–$C_6$) alkyl, ($C_1$–$C_6$) alkoxy, amino and trifluoromethyl; with an N-dealkylating agent.

11. The process of claim 10 wherein R is phenyl.

12. The process of claim 10 wherein R is hydrogen.

13. The process of claim 12 wherein R is ($C_6$–$C_{10}$)aryl and the dealkylating agent is α-chloroethyl chloroformate.

14. The process of claim 10 wherein the compound of formula V is prepared by treating a compound of the formula

VI

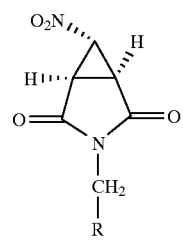

with a reducing agent.

15. The process of claim 14 wherein a compound of formula VI is prepared by treating a compound of the formula

VII

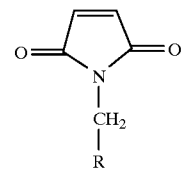

wherein R is selected from hydrogen ($C_1$–$C_6$) alkyl or ($C_6$–$C_{10}$)aryl wherein said aryl group may be substituted, optionally, with one or more substituents independently selected from halo, nitro, ($C_1$–$C_6$) alkyl, ($C_1$–$C_6$) alkoxy, amino and trifluoromethyl; with a compound of the formula X—$CH_2$—$NO_2$, wherein X is a leaving group, in the presence of 1,2-dimethyl-1,4,5,6-tetrahydropyrimidine.

16. The process according to claim 15 wherein R is ($C_6$–$C_{10}$).

17. The process according to claim 15 wherein R is hydrogen.

18. The process according to claim 15, wherein X is chloro or bromo.

19. The process according to claim 18 wherein X is bromo.

20. The process according to claim 15 wherein said process is carried out at a temperature from about −78° C. to about 80° C.

21. The process according to claim 15 wherein said process is carried out in a solvent selected from benzene, toluene, dimethylformamide or tetrahydrofuran.

22. the process according to claim 21 wherein said solvent is toluene.

23. A process for the preparation of a compound of the formula I as defined in claim 1 which comprises the steps of a) treating a compound of the formula VII as defined in claim 15 with a compound of the formula X—$CH_2$—$NO_2$, wherein X is a leaving group, in the presence of a base to form a compound of the formula VI and treating the resultant compound of formula VI as defined in claim 14 with a reducing agent to form the compound of the formula V as defined in claim 10;

b) treating the compound of the formula V with a dealkylating agent to form the compound of formula IV as defined in claim 6;

c) treating the compound of formula IV with a compound of the formula

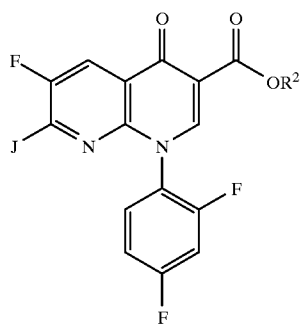

wherein R² is as defined in claim 1 and J is a leaving group, in the presence of a base to form a compound of the formula II as defined in claim 1;
and then treating the compound of the formula II with
(1) a metal and an acid of the formula R¹H, as defined above, to form directly the compound of formula I; or
(2) a reducing agent of either
(i) a metal and an acid of the formula R¹H, as defined above, to form the compound of the formula

IIIA

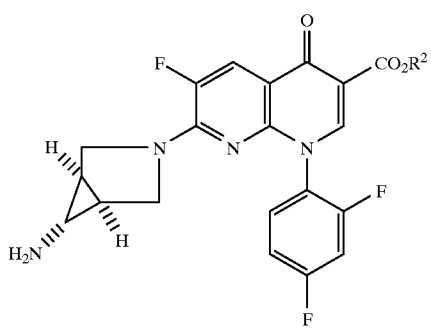

or
(ii) hydrogen in the presence of a catalyst to form the compound of the formula IIIA, and then treating the compound of the formula IIIA, formed in steps (i) or (ii) above with a compound of the formula R¹H, which may be the same as or different from the R¹H of the reducing step, to form the compound of the formula I.

24. The process of step a) of claim 23 wherein said base is 1,2-dimethyl-1,4,5,6-tetrahydropyrimidine.

25. The process of step d) of claim 23 wherein the acid is an alkanesulfonic acid.

26. The process of claim 25 wherein said acid is methanesulfonic acid.

27. The process of claim 23 wherein said metal is zinc.

28. A compound of the formula

IV

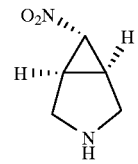

29. A compound of the formula

III B

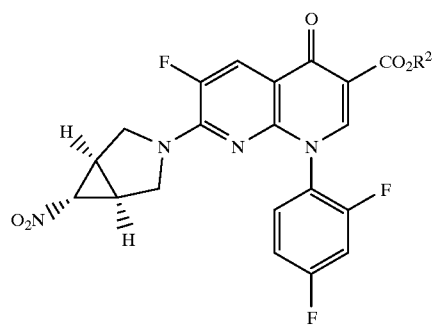

wherein R² is as defined as in claim 1.

30. The process of claim 1 wherein the reducing agent is selected from the group consisting of a) the combination of a metal and an acid of the formula R¹H as defined in claim 1, or b) hydrogen over Raney nickel.

31. The process of step d) ii) of claim 23 wherein the reducing agent is selected from the group consisting of a) the combination of a metal and an acid of the formula R¹H as defined as above, or b) hydrogen over Raney nickel.

32. The process of claim 10 wherein the dealkylating agent is hydrogen or α-chloroethyl chloroformate when R is $(C_6-C_{10})$aryl or the dealkylating agent is α-chloroethyl chloroformate when R is hydrogen or $(C_1-C_6)$alkyl.

33. The process of step b) of claim 23 wherein the dealkylating agent is hydrogen or α-chloroethyl chloroformate when R is $(C_6-C_{10})$aryl or the dealkylating agent is α-chloroethyl chloroformate when R is hydrogen or $(C_1-C_6)$alkyl.

* * * * *